United States Patent
Lee et al.

(10) Patent No.: US 10,577,192 B2
(45) Date of Patent: Mar. 3, 2020

(54) ROTATING TABLET TRANSFER APPARATUS WITH PRESSURED SPACES

(71) Applicant: ENCLONY INC, Seoul (KR)

(72) Inventors: Kyung-Ho Lee, Seoul (KR); Byung-In Kim, Seoul (KR)

(73) Assignee: ENCLONY INC, Seoul (KR)

( * ) Notice: Subject to any disclaimer, the term of this patent is extended or adjusted under 35 U.S.C. 154(b) by 220 days.

(21) Appl. No.: 15/567,144

(22) PCT Filed: Apr. 14, 2016

(86) PCT No.: PCT/KR2016/003897
§ 371 (c)(1),
(2) Date: Oct. 17, 2017

(87) PCT Pub. No.: WO2016/167572
PCT Pub. Date: Oct. 20, 2016

(65) Prior Publication Data
US 2018/0100813 A1    Apr. 12, 2018

(30) Foreign Application Priority Data

Apr. 17, 2015  (KR) .................. 10-2015-0054635

(51) Int. Cl.
  *B65G 47/84*  (2006.01)
  *G01N 21/85*  (2006.01)
  *G01N 21/95*  (2006.01)

(52) U.S. Cl.
  CPC ...... *B65G 47/848* (2013.01); *B65G 2201/027* (2013.01); *G01N 21/85* (2013.01); *G01N 21/9508* (2013.01)

(58) Field of Classification Search
  CPC .......... B65G 2201/027; B65G 47/1457; B65G 47/14; B65G 47/848; B65G 47/1428;
  (Continued)

(56) References Cited

U.S. PATENT DOCUMENTS 3,770,164 A  *  11/1973  Hembree ................. A01C 1/06
                                                    221/211
4,354,602 A  *  10/1982  Miyoshi .................... B07C 5/36
                                                    209/545
(Continued)

FOREIGN PATENT DOCUMENTS

JP    60-72418 U    5/1985
JP    01-193630 A   8/1989
(Continued)

OTHER PUBLICATIONS

Machine Translation JP2005289584 (Year: 2019).*
(Continued)

*Primary Examiner* — Peter J Macchiarolo
*Assistant Examiner* — David L Singer
(74) *Attorney, Agent, or Firm* — Renner, Otto, Boisselle & Sklar, LLP (57) ABSTRACT

A tablet transfer apparatus includes a fixed plate provided with a rotary shaft penetrating therethrough, a negative pressure space formed therein to allow negative pressure to be partially applied to the negative pressure space, and a suction hole communicating at least with the negative pressure space; and a rotary plate combined with the rotary shaft to rotate, and provided with a concave groove formed in a circumferential surface of the rotary plate to communicate with the negative pressure space.

8 Claims, 5 Drawing Sheets

(58) Field of Classification Search
CPC ...... G01N 21/9508; B65B 1/16; B65B 35/28; B65B 5/103; B07C 5/365
See application file for complete search history.

(56) References Cited

U.S. PATENT DOCUMENTS

| | | | | |
|---|---|---|---|---|
| 4,757,382 | A * | 7/1988 | Kaziura | B65G 21/2036 198/689.1 |
| 5,232,079 | A * | 8/1993 | Belcastro | A24C 5/34 198/370.11 |
| 5,661,249 | A * | 8/1997 | Rupp | B07C 5/36 73/45 |
| 6,079,284 | A | 6/2000 | Yamamoto et al. | |
| 6,556,295 | B2 | 4/2003 | Leide et al. | |
| 6,741,731 | B1 * | 5/2004 | Yamamoto | G01N 21/9508 382/141 |
| 6,886,683 | B1 | 5/2005 | Kakiuchi et al. | |
| 2007/0289660 | A1 * | 12/2007 | Aylward | B65B 5/103 141/18 |
| 2008/0061074 | A1 * | 3/2008 | Remis | B65B 5/103 221/69 |
| 2012/0293649 | A1 * | 11/2012 | Nygaard | G01N 21/9508 348/91 |
| 2013/0022250 | A1 * | 1/2013 | Nygaard | A61J 3/007 382/128 |

FOREIGN PATENT DOCUMENTS

| | | |
|---|---|---|
| JP | 03-042415 A | 2/1991 |
| JP | 11-51873 A | 2/1999 |
| JP | 2001-97550 A | 4/2001 |
| JP | 2005-289584 A | 10/2005 |
| JP | 2007-246214 A | 9/2007 |
| JP | 2008-241342 A | 10/2008 |
| JP | 2011-156514 A | 8/2011 |
| KR | 10-0775178 B1 | 11/2007 |
| WO | WO-0123110 A1 * | 4/2001 ......... B65G 47/1485 |

OTHER PUBLICATIONS

STIC Human Translation JP 60-72418 U (Year: 2019).*
Machine Translation JPH0342415 (Year: 2019).*
Translation of Written Opinion for corresponding Patent Application No. PCT/KR2016/003897 dated Jul. 25, 2016. (Year: 2016).*
International Search Report and Written Opinion for corresponding Patent Application No. PCT/KR2016/003897 dated Jul. 25, 2016.
Japanese Office Action for corresponding Japanese Application No. JP 2018-506066 dated Feb. 5, 2019.

* cited by examiner

ROTATING TABLET TRANSFER APPARATUS WITH PRESSURED SPACES

TECHNICAL FIELD

The present disclosure relates to a tablet transfer apparatus, capable of inspecting the appearance of a tablet, while sequentially holding and transferring the tablet in a circumferential direction, irrespective of a feed interval during a rotary operation.

BACKGROUND ART

In general, tablets having capsule-type, elliptical or circular cross-sections have been produced in large quantities through automated processes, resulting in defective products during a process in which the tablets are discharged, rather than failure due to a component or dose.

Accordingly, there has been demand for a process of inspecting external defects, such as the adhesion or contamination of foreign matter, cracks or partial damage due to contact or impact between tablets, deformation or printing defects, or the like.

The process of inspecting the appearance of tablets is changing from a visual inspection performed by operators to an automatic inspection using automatic inspection apparatuses. Various types of automatic inspection devices for such automatic inspection have been proposed.

When automatically inspecting tablets using an automatic inspecting apparatus, a method, in which images of one sides of the tablets may be obtained by imaging the tablets using an imaging device during transfer of the tablets, and in which the other sides of the tablets are imaged using the imaging device during reversing positions of the tablets while being transferred, images of one side surfaces and the other side surfaces of the tablets subsequently being processed, thereby inspecting the existence or nonexistence of defects, has generally been adopted.

An example of such a technique is disclosed in Japanese Patent Laid-Open Publication No. 11-51873, relating to an apparatus for inspecting an appearance of a tablet, in which suction grooves or receiving grooves for holding tablets are formed in a circumferential surface of a transfer drum with predetermined intervals therebetween. Such an appearance inspection apparatus needs to have tablets supplied at a constant speed and interval by a supply unit in order to supply the tablets to the suction grooves formed at regular intervals around the transfer drum.

Thus, it may be difficult and complicated to precisely match a rotation speed of the transfer drum and the feed speed and interval in the supply unit. In detail, it may also be difficult to change the inspection speed depending on the shape of tablets or the difficulty of the inspection.

DISCLOSURE

Technical Problem

An aspect of the present disclosure is to provide a tablet transfer device capable of inspecting the appearance of a tablet while sequentially holding and transferring the tablet in a circumferential direction, irrespective of a feed interval during a rotary operation.

DISCLOSURE

Technical Solution

According to an aspect of the present disclosure, a tablet transfer apparatus includes a fixed plate provided with a rotary shaft penetrating therethrough, a negative pressure space formed therein to allow negative pressure to be partially applied to the negative pressure space, and a suction hole communicating at least with the negative pressure space; and a rotary plate combined with the rotary shaft to rotate, and provided with a concave groove formed in a circumferential surface of the rotary plate to communicate with the negative pressure space.

Advantageous Effects

As described above, according to an exemplary embodiment in the present disclosure, even when a large amount of tablets are supplied, the external appearance of tablets may be inspected while the tablets may be reliably sequentially held and transferred in line in a circumferential direction, regardless of a feed interval.

BEST MODE

Hereinafter, embodiments of the present disclosure will be described as follows with reference to the accompanying drawings. In adding reference numerals to constituent elements of respective drawings, the same constituent elements are denoted by the same reference numerals, even in the case in which they are shown indifferent drawings. In the following description of the present disclosure, a detailed description of functions and configurations below, known in the art, will be omitted in a case in which a subject matter of the invention is rather unclear.

Figure 1:
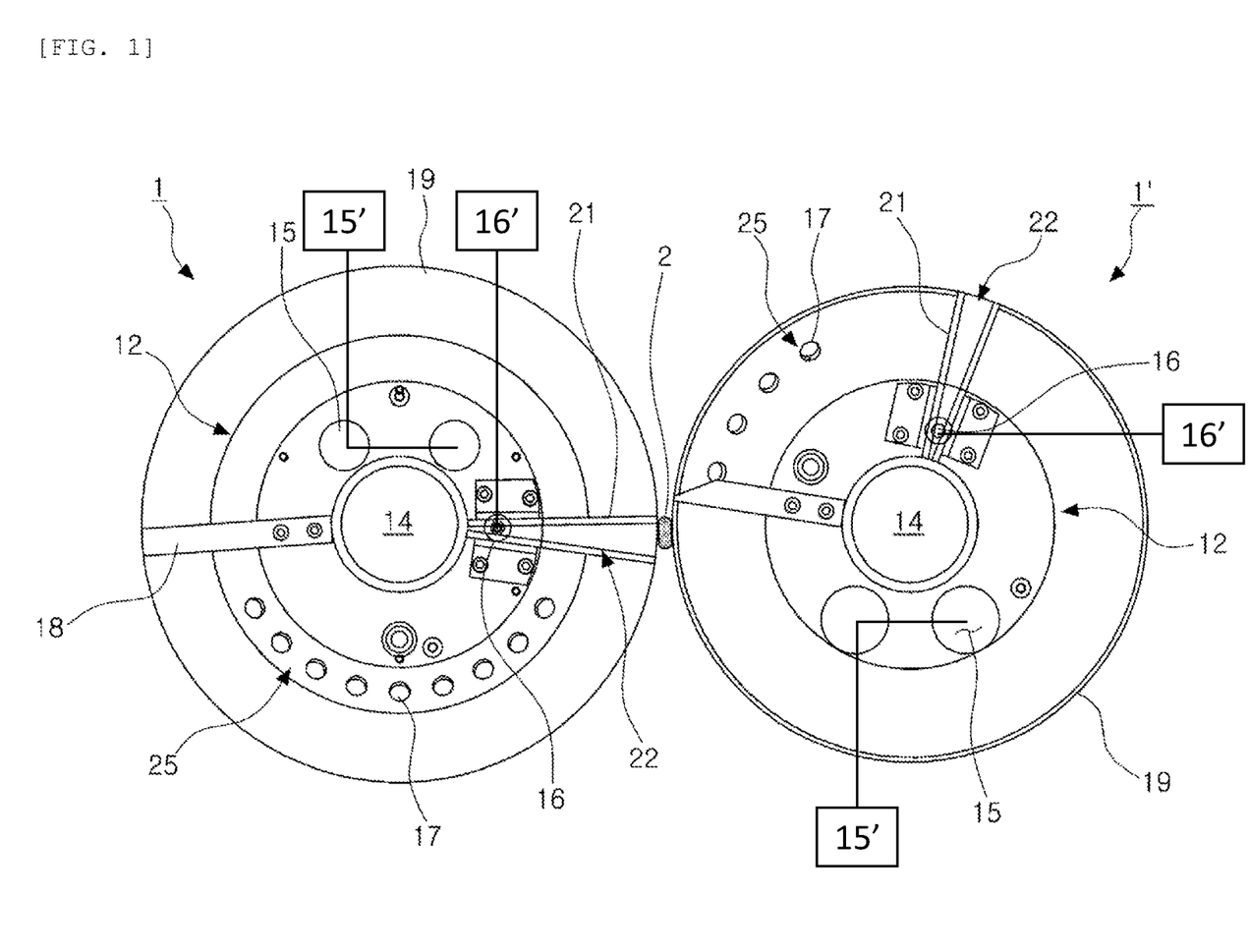
FIG. 1 is a plan cross-sectional view illustrating a layout state of a tablet transfer apparatus according to an exemplary embodiment in the present disclosure.
Figure 2:
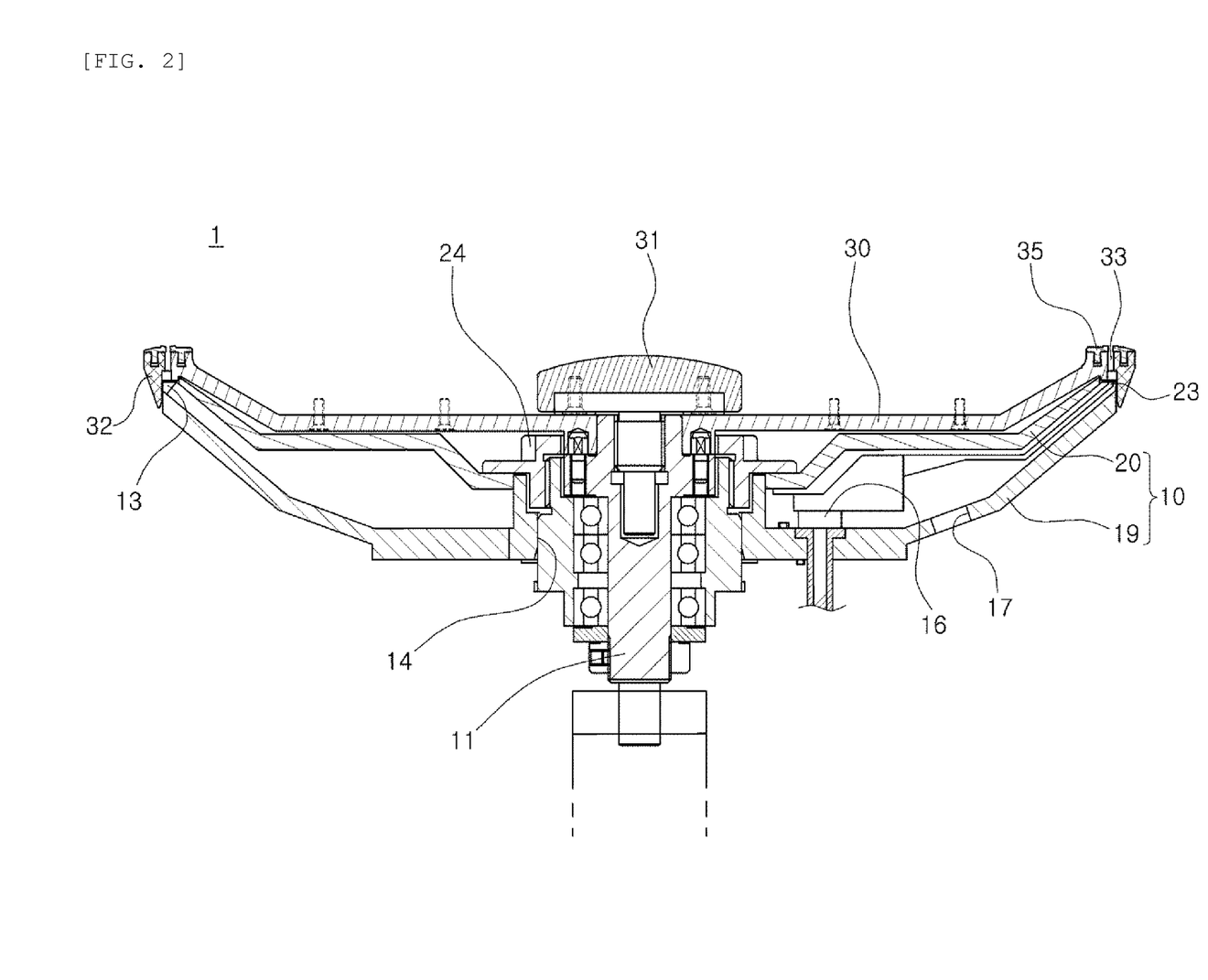
FIG. 2 is an assembled cross-sectional view illustrating an example of a tablet transfer apparatus according to an exemplary embodiment in the present disclosure.
Figure 3:
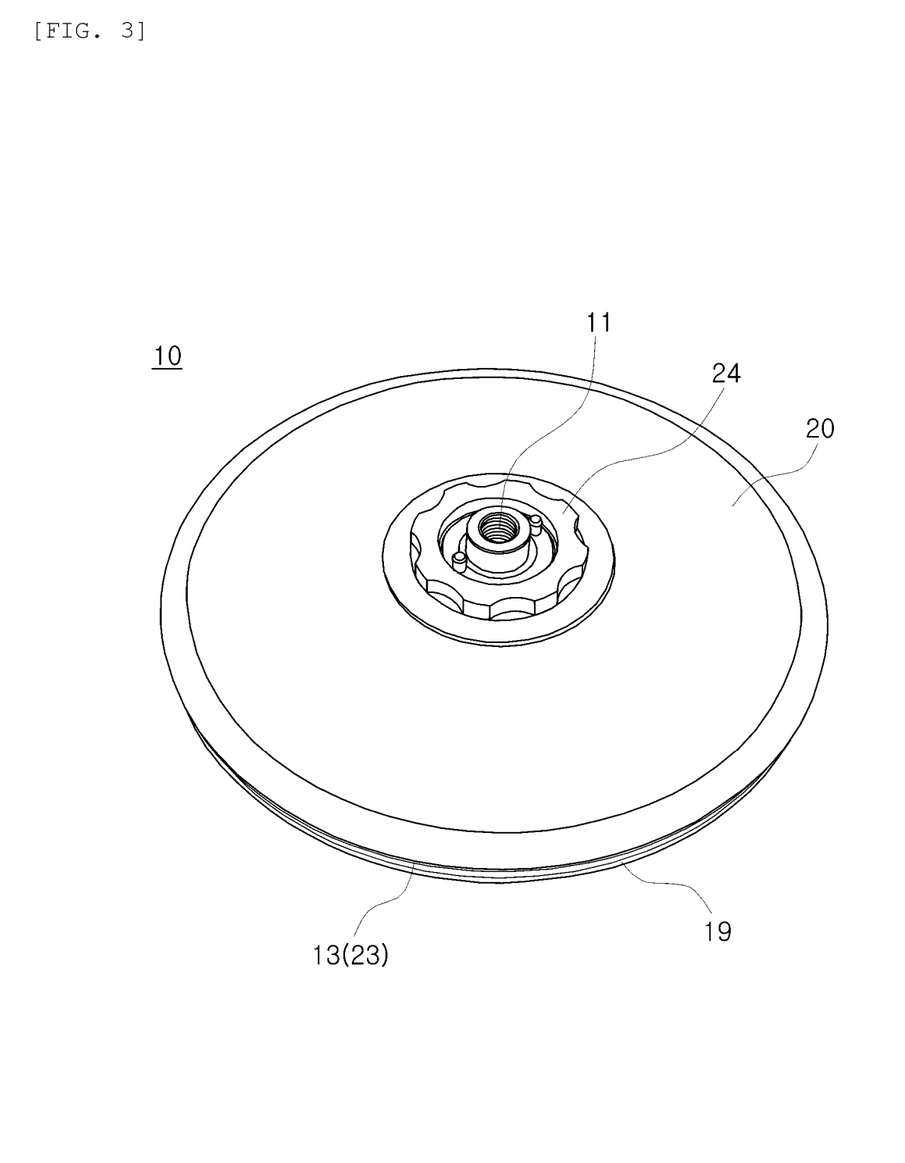
FIG. 3 is a perspective view of a fixed plate of a tablet transfer apparatus according to an exemplary embodiment in the present disclosure.

FIG. 1 is a plan cross-sectional view illustrating a layout state of a tablet transfer apparatus according to an exemplary embodiment, FIG. 2 is an assembled cross-sectional view illustrating an example of a tablet transfer apparatus according to an exemplary embodiment, and FIG. 3 is a perspective view of a fixed plate of a tablet transfer apparatus according to an exemplary embodiment.

As illustrated in the drawings, a tablet transfer apparatus 1 according to an exemplary embodiment may include a fixed plate 10, through which a rotary shaft 11 penetrates, in which a negative pressure space 12, allowing negative pressure to be partially applied inside thereof, is formed, and in which a suction hole 13 communicating at least with the negative pressure space 12; and a rotary plate 30 combined with the rotary shaft to rotate, and provided with a concave groove 33 formed in a circumferential surface thereof to communicate with the negative pressure space.

A tablet 2 used in the tablet transfer apparatus 1 according to an exemplary embodiment may be, for example, a pill or capsule-type tablet, or the like.

The tablet transfer apparatus 1, according to an exemplary embodiment, may be provided in such a manner that the tablet transfer apparatus may image appearances of tablets using an imaging device, while sequentially holding and transferring the tablets supplied in line by a supply unit (not shown), in a circumferential direction, regardless of a feed interval.

The fixed plate 10 may include a fixed-plate body 19 including a first through hole 14 through which the rotary shaft 11 penetrates, a second through hole 15 connected to a negative pressure device 15' such as an external vacuum suction device, a vacuum pump or the like to form the negative pressure space 12, and at least one blocking block 18 allowing for partition into the negative pressure space and a remaining region; and a fixed-plate cover 20 spaced apart from the fixed-plate body in at least the negative pressure space to form the suction hole 13, while being combined with the fixed-plate body.

The fixed-plate body 19 may be fixedly mounted on, for example, a support member of an automatic inspection apparatus, or the like.

In order to prevent interference of suction force, which may occur due to incomplete sealing between a negative pressure space and a remaining space to which negative pressure is not applied, together with smooth detachment of a tablet from a required location by a remaining region to which negative pressure is not applied after the tablet 2 is held and transferred by the negative pressure space; the fixed-plate body 19 may further include at least one third through hole 17 communicating with external air. Thus, atmospheric pressure may be applied to at least a portion of the remaining region to which the negative pressure is not applied, and thus, an atmospheric pressure space 25 may be formed.

In addition, in the fixed-plate body 19, a fourth through hole 16, surrounded by a blocking wall 21 and connected to a positive pressure device 16', such as an external air pump or the like, provided therein, may further be formed to form a positive pressure space 22, to which positive pressure is applied, in a portion of the remaining region to which negative pressure is not applied. At this time, the fixed-plate cover 20 may also be spaced apart from the fixed-plate body in the remaining region to which the negative pressure is not applied, to form a discharge hole 23.

As at least one of the third through hole 17 or the fourth through hole 16 is provided in the remaining region of the fixed-plate body 19, to which the negative pressure is not applied, the tablet 2 may be smoothly detached from a required position.

The fixed-plate cover 20 may be provided with, for example, a through hole 24 having a threaded portion formed therein, to be screw-combined with a threaded portion protruding around the first through hole 14 of the fixed-plate body 19. The rotary shaft 11 may penetrate through the through hole.

The fixed-plate cover 20 may be configured in such a manner that one surface thereof, constituting an inner surface of the fixed plate 10, may be in close contact with a front end face of the blocking block 18 or the blocking wall 21 of the fixed-plate body 19, to allow for partition into the negative pressure space and the remaining region. In detail, for example, when one side of the fixed-plate cover contacts the blocking block 18 and the other side thereof, separated by a predetermined angle therefrom, comes into contact with a different blocking block or the blocking wall 21, the atmospheric pressure space 25 to which atmospheric pressure is applied may be formed by the at least one third through-hole 17 communicating with external air.

In addition, as the fixed-plate cover contacts a front end surface of the blocking wall 21, the positive pressure space 22 to which positive pressure is applied may be formed through the fourth through-hole 16 connected to a positive pressure device.

Thus, negative pressure or attractive force may be formed in a portion of a front end of the fixed plate 10 by the suction hole 13, and positive pressure or repulsive force may be formed in a portion of the remaining front end by the discharge hole 23. In this case, since the fixed plate is fixedly provided, the negative pressure and the positive pressure, or the attractive force and the repulsive force, may be formed in a constant position.

Figure 4:
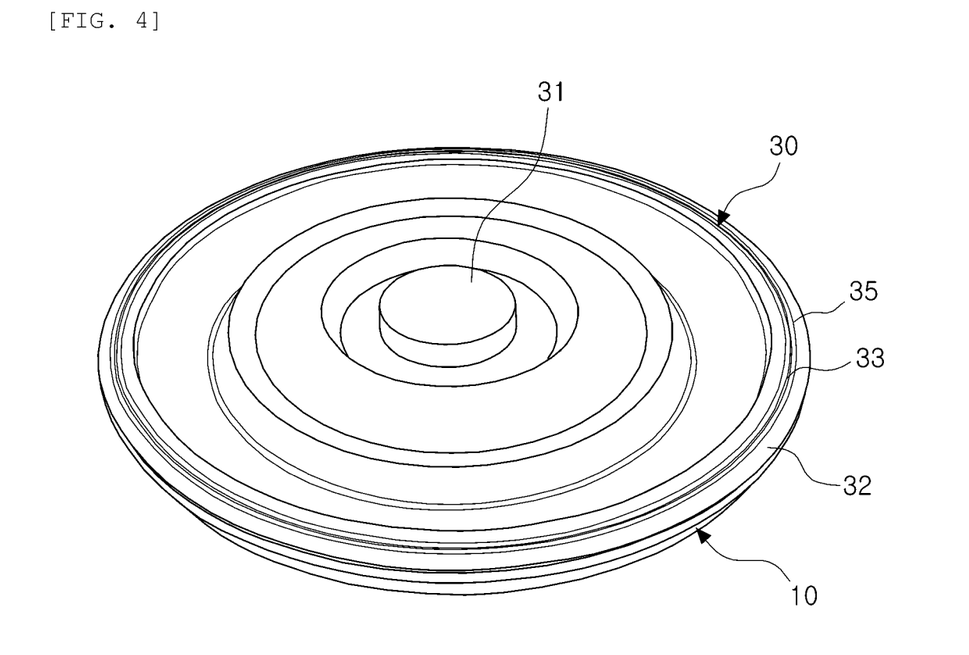
FIG. 4 is a perspective view illustrating a state in which a rotary plate is combined with the fixed plate of FIG. 3.

FIG. 4 is a perspective view illustrating a state in which a rotary plate is combined with the fixed plate of FIG. 3.

The rotary plate 30 may be coupled to the rotary shaft 11 by a coupling screw 31. The rotary shaft may be connected to a driving unit such as a motor, not shown, to rotate. The rotary plate may be formed to cover one surface of the fixed plate 10, and an outer circumferential end portion of the rotary plate may be bent toward the fixed plate to form an extended portion 32. In this case, the extended portion may shield an end surface of the fixed plate.

The concave groove 33 may be formed in the extended portion 32 to be disposed along a circumferential surface of the rotary plate 30. The plurality of communication holes 34, which may communicate with the suction hole 13 or the discharge hole 23 while being rotated, may be formed in a side wall of the concave groove with a predetermined intervals therebetween.

A pair of seating members 35 opposing each other, with a predetermined clearance therebetween, may be attached to both sides of an opening of the concave groove 33, for example, to open front ends of both side walls of the concave groove. The seating members may be formed of an elastic material such as rubber or the like, to prevent the tablet 2 from being damaged due to impact, upon contact with the tablet.

In addition, since the seating members 35 is provided to reduce an opening area of the concave groove 33 formed in the circumferential surface, a predetermined section in the concave groove may be formed as a section to which a negative pressure is applied, and the remaining section may be formed as a section to which atmospheric pressure or positive pressure is applied.

As such, the rotary plate 30 may rotate while covering one surface of the fixed plate 10, negative pressure may be applied into the concave groove in a position communicating with the suction hole 13 of the fixed plate through the communication holes 34 of the concave groove 33 formed in the circumferential surface along the extended portion 32 of the rotary plate, and positive pressure may be applied to the concave groove in a position communicating with the discharge hole 23 of the fixed plate.

Thus, in the section to which the negative pressure is applied, the tablet 2 may be supported while being held by the seating member 35 provided on the concave groove 33 formed along the circumferential surface of the rotary plate 30, and may be sequentially rotated together with the rotary plate to be transferred. A position of the tablet held by the seating member may not necessarily correspond to a position of the communication hole 34 and may be aligned in a row in the concave groove on the circumferential surface with an irregular interval therebetween.

Subsequently, for example, when the tablet 2 reaches a required position, for example, an end point of the section to which the negative pressure is applied or a start point of the section to which the positive pressure is applied instead of the negative pressure, the tablet may be released from the seating member 35 to be discharged. At this time, the positive pressure may be set to be greater than the negative pressure.

Although FIGS. 2 and 4 illustrate an example in which the concave groove 33 or the seating member 35 is disposed on an upper surface of the extended portion 32, the position of the concave groove or the seating member is not limited thereto.

Figure 5:
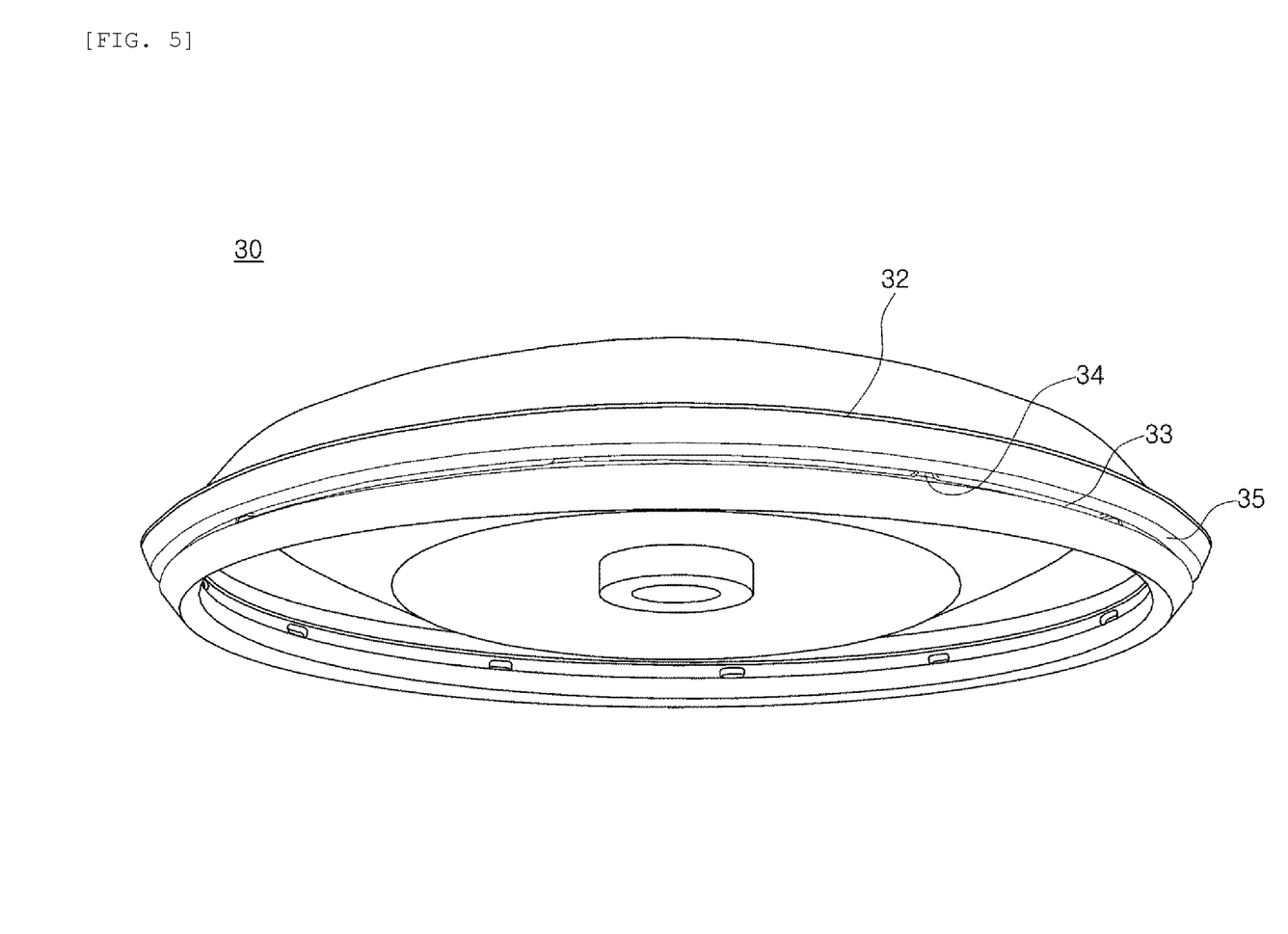
FIG. 5 is a perspective view illustrating a modified example of the rotary plate.

For example, as illustrated in FIG. 5, the concave groove 33 or the seating member 35 may be disposed on a lower surface of the extended portion 32 or on a downwardly inclined surface thereof.

In detail, a first tablet transfer apparatus in which the concave groove 33 holding the tablet 2 is located in an upper surface side of the rotary plate 30, and a second tablet transfer apparatus in which the concave groove holding the tablet is located in a lower surface side of the rotary plate, may be combined.

By using the combination as described above as illustrated in FIG. 1, the tablet 2 may be sequentially conveyed while being held by holding force acting in a first tablet transfer apparatus 1 in the circumferential direction, and at this time, an image of one side of the tablet may be captured to be inspected using a first camera (not shown) installed on one side.

In addition, a second tablet transfer apparatus 1', in which the position of the concave groove 33 is reversed, while having the same as or a similar configuration to that of the first tablet transfer apparatus, may be disposed to be close to the first tablet transfer apparatus 1, such that the second tablet transfer apparatus may hold the tablet 2 in a state in which the tablet transferred to the first tablet transfer apparatus is reversed.

For example, when the tablet 2 is transferred to the second tablet transfer apparatus 1', positive pressure to release the tablet 2 through a discharge hole or the like may be generated in the first tablet transfer apparatus 1, or the generation of holding force may be stopped by atmospheric pressure such that the tablet may be smoothly held by the second tablet transfer apparatus without interference.

An image of the other side of the tablet 2 conveyed in the reversed state in the second tablet transfer apparatus 1' may be captured using a second camera (not shown) installed on one side of the second tablet transfer apparatus, thereby performing an inspection of the tablet.

In addition, the tablet having been completed in the inspection may be detached or dropped from the second tablet transfer apparatus 1' and may be discharged.

The concave groove 33 or the seating member 35 may also be disposed on a side of the extended portion 32, for example, on a front end surface thereof provided toward a side of the rotary plate 30, as well as an upper surface or a lower surface of the extended portion 32. In detail, in the case of the tablet transfer apparatus 1 according to an exemplary embodiment, the concave groove or the seating member may be located in a proper position of the extended portion as long as the tablet 2 may be held by the negative pressure along a circumferential surface edge of a rotary plate having a disk shape.

While exemplary embodiments have been shown and described above, it will be apparent to those skilled in the art that modifications and variations could be made without departing from the scope of the present invention as defined by the appended claims. Therefore, the embodiments disclosed in the present invention are not intended to limit the scope of the present invention but to limit the scope of the technical idea of the present invention. The scope of protection of the present invention should be construed according to the following claims, and all technical ideas within the scope of equivalents thereof should be construed as being included in the scope of the present invention.

The invention claimed is:

1. A tablet transfer apparatus comprising:
    a fixed plate provided with a rotary shaft penetrating therethrough, a negative pressure space formed therein to allow negative pressure to be partially applied to the negative pressure space, and a suction hole communicating at least with the negative pressure space; and
    a rotary plate combined with the rotary shaft to rotate, and provided with a concave groove formed in a circumferential surface of the rotary plate to communicate with the negative pressure space,
    wherein the fixed plate further comprises
        a fixed-plate body including a first through hole through which the rotary shaft penetrates, a second through hole connected to an external negative pressure device to form the negative pressure space, and at least one blocking block allowing for partition into the negative pressure space and a remaining region; and
        a fixed-plate cover spaced apart from the fixed-plate body in at least the negative pressure space to form the suction hole, while being combined with the fixed-plate body,
    wherein in the fixed-plate body, at least one third through hole communicating with external air is further formed in the remaining region to which negative pressure is not applied so as to form an atmospheric pressure space,
    wherein the fixed-plate cover is configured in such a manner that one surface thereof is in contact with the at least one blocking block of the fixed-plate body to allow for partition into the negative pressure space and the atmospheric pressure space,
    wherein in the fixed-plate body, a fourth through hole connected to an external positive pressure device while being surrounded by a blocking wall may further be formed to form a positive pressure space, to which positive pressure is applied, in a portion of the remaining region to which negative pressure is not applied,
    so that the negative pressure space, the positive pressure space, and the atmospheric pressure space are sequentially arranged in the rotation direction of the rotary plate.

2. The tablet transfer apparatus of claim 1, wherein in the positive pressure space, the fixed-plate cover is spaced apart from the fixed-plate body to form a discharge hole.

3. The tablet transfer apparatus of claim 1, wherein one surface of the fixed-plate cover contacts the blocking wall of the fixed-plate body to form the positive pressure space.

4. The tablet transfer apparatus of claim 1, wherein the rotary plate is configured to cover one surface of the fixed plate, and an outer circumferential end portion of the rotary plate is bent toward the fixed plate to form an extended portion.

5. The tablet transfer apparatus of claim 4, wherein in the extended portion, a plurality of communication holes are disposed in a side wall of the concave groove.

6. The tablet transfer apparatus of claim 5, wherein an opening of the concave groove is provided with seating members formed of an elastic material, opposing each other, and attached to two sides of the opening of the concave groove.

7. The tablet transfer apparatus of claim 6, wherein when the tablet transfer apparatus is provided as a plurality of tablet transfer apparatuses combined with each other, one of the plurality of tablet transfer apparatuses is provided with the concave groove formed in one side of the rotary plate, and the other tablet transfer apparatus is provided with a second concave groove formed in the other side of the rotary plate.

8. The tablet transfer apparatus of claim 6, wherein when the tablet transfer apparatus is provided as a plurality of tablet transfer apparatuses combined with each other, the tablet transfer apparatus is provided with the concave groove disposed in a front end surface of the rotary plate provided toward a side of the rotary plate.

* * * * *